United States Patent
Fougere et al.

(10) Patent No.: US 10,105,101 B2
(45) Date of Patent: Oct. 23, 2018

(54) METHODS, SYSTEMS, AND DEVICES FOR OPTIMAL POSITIONING OF SENSORS

(71) Applicant: LifeScan, Inc., Wayne, PA (US)

(72) Inventors: Richard Fougere, Washington Crossing, PA (US); Curtis Lee, Philadelphia, PA (US); Ryan Walsh, Douglassville, PA (US)

(73) Assignee: LifeScan, Inc., Wayne, PA (US)

( * ) Notice: Subject to any disclaimer, the term of this patent is extended or adjusted under 35 U.S.C. 154(b) by 177 days.

(21) Appl. No.: 15/108,588

(22) PCT Filed: Dec. 23, 2014

(86) PCT No.: PCT/US2014/072298
§ 371 (c)(1),
(2) Date: Jun. 28, 2016

(87) PCT Pub. No.: WO2015/103061
PCT Pub. Date: Jul. 9, 2015

(65) Prior Publication Data
US 2016/0317088 A1    Nov. 3, 2016

Related U.S. Application Data

(60) Provisional application No. 61/922,097, filed on Dec. 31, 2013.

(51) Int. Cl.
*A61B 5/00*    (2006.01)
*A61B 5/0205*  (2006.01)
(Continued)

(52) U.S. Cl.
CPC ............ *A61B 5/684* (2013.01); *A61B 5/0002* (2013.01); *A61B 5/0006* (2013.01);
(Continued)

(58) Field of Classification Search
CPC ... A61B 5/0002; A61B 5/0006; A61B 5/0008; A61B 5/02055; A61B 5/021;
(Continued)

(56) References Cited

U.S. PATENT DOCUMENTS 5,494,043 A    2/1996  O'Sullivan et al.
2006/0030781 A1*  2/2006  Shennib ............... A61B 5/0402
                                            600/509

(Continued)

FOREIGN PATENT DOCUMENTS

WO    20100134010 A1    11/2010
WO    2013076656 A1     5/2013

OTHER PUBLICATIONS

Supplementary European Search Report issued in related European Patent Application No. 14876345.1, dated Jul. 5, 2017, 9 pages.

(Continued)

*Primary Examiner* — Michael Carey

(57) ABSTRACT

A biomedical sensor has conducting elements disposed at least partly over a skin-facing surface. A sensing element detects a signal representative of a physiological parameter of a body using the conducting elements. A storage device stores a physiological model. A processor determines sensor placement quality by comparing the signal to the model and operates an indicator to indicate the determined quality. A method of measuring using the sensor includes computing a measurement acceptance criterion using numerous measurements, determining whether a subsequent test measurement corresponds to the measurement acceptance criterion obtained from the computing step, and indicating the results via the indicator. A system for measuring a physiological property of the body includes the sensor, a user interface device to receive measurements from the sensor, and a processor associated with the user interface device and (Continued)

configured to provide feedback if the measurement does not meet a selected acceptance criterion.

18 Claims, 7 Drawing Sheets

(51) Int. Cl.
| | | |
|---|---|---|
| *A61B 5/06* | (2006.01) | |
| *A61B 5/024* | (2006.01) | |
| *A61B 5/0478* | (2006.01) | |
| *A61B 5/0488* | (2006.01) | |
| *A61B 5/053* | (2006.01) | |
| *A61B 5/021* | (2006.01) | |
| *A61B 5/145* | (2006.01) | |

(52) U.S. Cl.
CPC ........ *A61B 5/0008* (2013.01); *A61B 5/02055* (2013.01); *A61B 5/053* (2013.01); *A61B 5/0531* (2013.01); *A61B 5/065* (2013.01); *A61B 5/742* (2013.01); *A61B 5/021* (2013.01); *A61B 5/024* (2013.01); *A61B 5/02405* (2013.01); *A61B 5/0478* (2013.01); *A61B 5/0488* (2013.01); *A61B 5/0533* (2013.01); *A61B 5/14532* (2013.01); *A61B 5/6844* (2013.01); *A61B 2560/0223* (2013.01)

(58) Field of Classification Search
CPC ... A61B 5/024; A61B 5/02405; A61B 5/0478; A61B 5/0488; A61B 5/053; A61B 5/0531; A61B 5/0533; A61B 5/065; A61B 5/14532; A61B 5/684; A61B 5/6844; A61B 5/742; A61B 2560/0223
USPC .................................................. 600/300, 301
See application file for complete search history.

(56) References Cited

U.S. PATENT DOCUMENTS

| | | |
|---|---|---|
| 2007/0060807 A1 | 3/2007 | Oishi |
| 2008/0221410 A1 | 9/2008 | Campbell et al. |
| 2008/0221414 A1 | 9/2008 | Baker |
| 2008/0221417 A1 | 9/2008 | Baker et al. |
| 2011/0245622 A1 | 10/2011 | McKenna |
| 2012/0203076 A1* | 8/2012 | Fatta ............... A61B 5/681 600/300 |

OTHER PUBLICATIONS

International Preliminary Report on Patentability issued in related International Patent Application No. PCT/US2014/072298, dated Jul. 5, 2016, 6 pages.

International Search Report and Written Opinion issued in related International Patent Application No. PCT/US2014/072298, dated Apr. 29, 2015, 9 pages.

* cited by examiner

METHODS, SYSTEMS, AND DEVICES FOR OPTIMAL POSITIONING OF SENSORS

PRIORITY

This application is the National Stage under Section 371 of International Patent Application No. PCT/US2014/072298 filed Dec. 23, 2014, which application claims the benefits of priority under the Paris Convention and 35 USC § 119 to prior filed U.S. Provisional Patent Application Ser. No. 61/922,097 filed on Dec. 31, 2013, which prior application are hereby incorporated by reference.

TECHNICAL FIELD

This application relates generally to the field of electronic systems for monitoring biological properties of a user's body, and more specifically to medical monitoring systems.

BACKGROUND

The use of various types of sensors to evaluate one or more physiological characteristics or parameters of a patient is well known. For example, optical pulse oximetry sensors measure the level of oxygen saturation ($SpO_2$) in a patient's blood. Typically, a light emitting diode (LED) transmits optical radiation of several different wavelengths, e.g., visible and infrared, through blood and tissue of a predetermined portion of a patient's body, such as the wrist or finger. A photodetector detects the light after it passes through the body. Different wavelengths of light are absorbed differently based on blood oxygen content, so detecting the optical attenuation at each wavelength permits the determination of oxygen saturation. In another example, electrocardiogram (ECG or EKG) electrodes are generally planar electrodes connected via wires to an ECG unit that measures the voltage across different pairs of the electrodes to monitor the patient's heart. It is generally required that sensors be correctly placed with respect to a specific body part to be measured. For example, an optical pulse oximetry sensor should be placed so that the optical path from the transmitter to the detector intersects a blood vessel. In like fashion, an ECG sensor should be placed on a part of the body that provides effective electrical contact across the skin (e.g., not on top of significant amounts of hair).

Sensors are constructed in different forms to enable attachment to different portions of a patient's body. For example, optical oximetry sensors can operate by detecting light transmitted through the tissue or light reflected by the tissue. Transmission-mode sensors are useful for fingers and other narrow parts of the body. Reflection-mode sensors are useful for thicker parts of the body, e.g., the forehead or torso. Moreover, sensors are generally calibrated relative to their intended usage. For example, optical sensors are designed and calibrated depending on whether their intended use is as a transmission or reflectance sensor, and will be calibrated for a specific spacing, or range of spacings, between the emitters and the detector. Thus, even two transmission sensors, such as one intended for use on a fingertip and another intended for use on an earlobe, will typically have different calibrations. The calibration differences between a transmission sensor and a reflectance sensor are typically greater.

Sensors are designed for specific locations on the body, as discussed above. Given this specificity, it can be difficult for caregivers to apply sensors correctly. This situation is exacerbated when patients must properly apply sensors to themselves, e.g., in outpatient or home-care situations. For example, a bandage-type transmission sensor intended for use on a fingertip, and which would normally be folded over or around the fingertip, may be unfolded and applied to another portion of the patient's body in a configuration like a reflectance sensor. However, in such a circumstance, not only are the placement of the sensor and measurement method different from what was intended, but the spacing between the emitters and detector is also significantly different from what was intended for the sensor. Thus, the misapplied sensor will not give accurate readings for the patient. Other misapplications of a sensor include placement on a site which, although positionally correct, is not suitable for optimal measurements. This situation may exist, for example, when the physical characteristics of the site are unsatisfactory to yield reliable measurements, e.g., due to sweat, hair, or position of subcutaneous fat. For example, although an oximeter calibrated for the pointer finger may be intended for use with either finger, differences between the patient's two pointer fingers may only permit the oximeter to be effectively used with one of those fingers. Moreover, the user or health care provider may unwittingly or carelessly position a physiologic sensor in whole or in part over an article of clothing.

SUMMARY OF THE DISCLOSURE

In one embodiment, therefore, a biomedical sensor has been devised. The biomedical sensor may include the following components:
 a) a sensor body having a skin-facing surface and an opposed surface;
 b) a plurality of conducting elements disposed at least partly over the skin-facing surface;
 c) a sensing element connected to the conducting elements, so that the sensing element detects a signal representative of a physiological parameter of a body facing the skin-facing surface using the conducting elements;
 d) an indicator spaced apart from the skin-facing surface;
 e) a storage device storing a physiological model; and
 f) a processor coupled to the sensing element, the indicator, and the storage device, so that the processor determines a quality of sensor placement by comparing the signal to the stored physiological model and operates the indicator to provide a human-perceptible indication of the determined quality.

In another embodiment, a method of determining optimal placement of a sensor on a user's body for measuring a physiological parameter of the user is provided. The method can be achieved by:
 a calibration step of measuring the physiological parameter of the body using a sensor a plurality of times to provide respective measurements;
 using a processor, automatically computing a measurement acceptance criterion using the respective measurements;
 a testing step of measuring the physiological parameter of the body using the sensor to provide a test measurement;
 automatically determining whether the test measurement corresponds to the measurement acceptance criterion obtained from the computing step; and
 automatically operating an indicator of the sensor to provide a human-perceptible indication of the results of the determining step.

In another embodiment, a system to determine optimal placement of a sensor on a user's body for measuring a physiological parameter of the user is provided. The system may include the following components:
   a) a sensor having a sensing element configured to measure the physiological parameter, and having a first transceiver configured to communicate the measurement;
   b) a user interface device including a second transceiver configured to receive the measurement from the first transceiver; and
   c) a processor associated with the user interface device and configured to automatically determine, using the received measurement, whether a sensor position over the body at a time corresponding to the received measurement meets a selected acceptance criterion, and, if not, to present sensor-position feedback to the user via, the user interface device.

Each of these embodiments, exemplary of the present invention, can provide improved feedback regarding sensor positioning. Various embodiments advantageously provide users and home-care providers ways of positioning sensors accurately. Various embodiments provide detection of conditions that may interfere with sensor readings.

Accordingly, in any of the embodiments described earlier, the following features may also be utilized in various combinations with the previously disclosed embodiments. For example, the biomedical sensor can include the indicator having plural separately-activatable visual indicators, in which the processor is configured to activate a selected number of the visual indicators to provide the human-perceptible indication, the selected number correlated with the determined quality. The processor can be configured to activate none of the visual indicators if the signal corresponds to an absence or failed detection of the physiological parameter; to activate a selected first positive number of the visual indicators if the signal is not consistent with the physiological model; and to activate a selected second positive number of the visual indicators if the signal is consistent with the physiological model, the selected second positive number being greater than the selected first positive number. The physiological parameter can be selected from the group consisting of blood pressure, pulse rate, skin conductance, galvanic skin response, temperature, electrocardiogram signal, blood glucose concentration, and heart rate variability. The sensor can include a motion sensor and a storage device storing a motion model corresponding to a selected location on the body, in which the processor is further configured to record motion data from the motion sensor, compare the recorded motion data to the stored motion model, and provide a human-perceptible indication of a result of the comparison. The processor can be configured to provide a human-perceptible indication of the selected location if the recorded motion data do not correspond to the stored motion model. The processor can be further configured to update the stored physiological model using the signal if the comparison indicates the detected physiological parameter corresponds to the stored physiological model.

In various examples, the method can include in which the calibration step may include presenting an indication via a user interface that the user should perform a specific action, and measuring the physiological parameter while the user performs the action. The operating step can include deactivating the sensor for a selected period of time if the test measurement does not correspond to the measurement acceptance criterion obtained from the computing step. The indicator can include plural separately-activatable visual indicators and the operating step can include activating a selected number of the visual indicators to provide the human-perceptible indication, the selected number correlated with the results of the determining step. The method can include presenting an indication of a sensor site on the body via a user interface; retrieving from a storage device a physiological model corresponding to the indicated sensor site; measuring the physiological parameter of the body using the sensor; automatically comparing the measured physiological parameter to the retrieved physiological model; and a second operating step of automatically operating the indicator to provide a human-perceptible indication of the result of the comparing step. The method can include, if the measured physiological parameter does not correspond to the retrieved physiological model, performing a recommending step of automatically determining a second sensor site on the body; and repeating the presenting-indication, retrieving, measuring, and comparing steps, and the second operating step, using the second sensor site. The method can include receiving via the user interface one or more user indication(s) of respective rating(s) of sensor placement(s) in respective region(s) of the body and storing the received user indication(s) in the storage device, the recommending step including determining the second sensor site using the stored user indication(s). The method can include receiving via the user interface an indication of a medical condition of the user and storing the indication in the storage device, the recommending step including determining the second sensor site using the stored indication.

The system can include the user interface device being separate from the sensor, and the first and second transceivers including radio-frequency communications transceivers. The user interface device can include a touchscreen configured to present the sensor-position feedback. The processor can be configured to receive a plurality of measurements from the sensor via the first and second transceivers and to concurrently present respective sensor-position feedback for each of the plurality of measurements via the user interface device. The system can include a storage device configured to store data representing the selected acceptance criterion.

In the aforementioned aspects of the disclosure, the steps of calibration, computing, testing, determining, operating, presenting, retrieving, measuring, comparing, operating (the second operating step), recommending, repeating, or receiving indications (possibly in conjunction with an equation) may be performed be an electronic circuit or a processor. These steps may also be implemented as executable instructions stored on a computer readable medium; the instructions, when executed by a computer may perform the steps of any one of the aforementioned methods.

In additional aspects of the disclosure, there are computer readable media, each medium comprising executable instructions, which, when executed by a computer, perform the steps of any one of the aforementioned methods.

In additional aspects of the disclosure, there are devices, such as sensors, or smartphones or other user-interface devices, each comprising an electronic circuit or processor configured to perform steps of any one of the aforementioned methods.

These and other embodiments, features and advantages will become apparent to those skilled in the art when taken with reference to the following more detailed description of various exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention. For the sake of clarity, like reference numerals herein represent like elements.

DETAILED DESCRIPTION

The following detailed description should be read with reference to the drawings, in which like elements in different drawings are identically numbered. The drawings, which are not necessarily to scale, depict selected embodiments and are not intended to limit the scope of the invention or the attached claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values not at least ±10% of the recited value, e.g. "about 90%" may refer to the range of values from 81% to 99%. As used herein, the phrase "electrical signal" or "signal" is intended to include direct current signals, alternating signals, or any signal within the electromagnetic spectrum. The terms "processor," "microprocessor," and "microcontroller" are intended to have the same meaning and are intended to be used interchangeably. Throughout this disclosure, the terms "patient" and "subject" are used interchangeably. These terms can refer to any human or animal subject and are not intended to limit the systems or methods to human use, although use of aspects described herein for a human patient represents a preferred embodiment. Furthermore, in this disclosure, the term "user" can refer to a patient using a biosensor or another person (e.g., a parent or guardian, nursing staff member, home care employee, or other caretaker) using such a device. The term "healthcare provider" or "HCP" refers generally to doctors, nurses, and individuals other than the patient that provide health care services to the patient.

Various embodiments described herein advantageously permit positioning a sensor for the measurement of physiologic sensor data without extensive or complicated sensor-placement processes. This permits measuring more-consistent, more-reliable sensor data, which in turn can improve user perceptions of the trust that can be placed in the system. As used herein, the term "sensor" refers to various types of sensors, including biosensors for obtaining physiological data of a patient.

Figure 1:
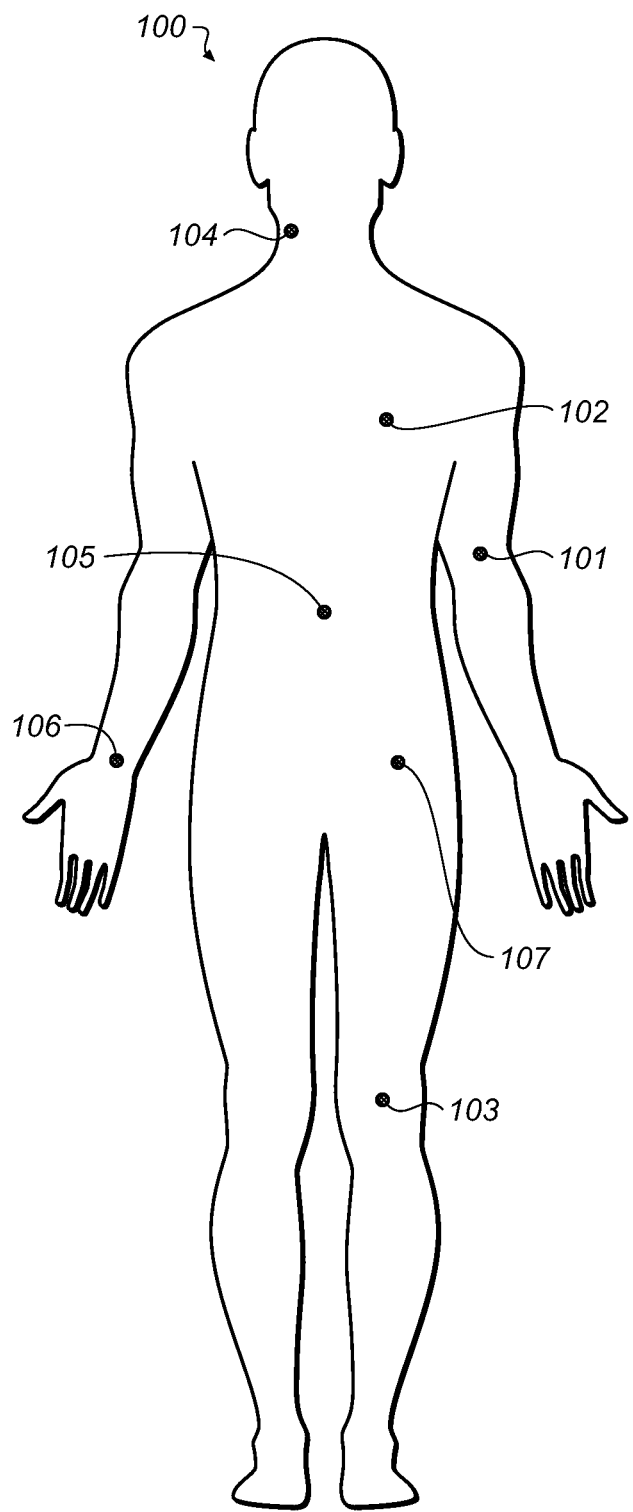
FIG. 1 is a graphical representation of a patient illustrating exemplary locations at which a sensor, such as a biosensor, can be placed.

FIG. 1 is a graphical representation of the body 100 of a patient illustrating exemplary locations at which a sensor, such as biosensor, can be placed for obtaining physiological parameter data. Locations 101, 102, 103, 104, 105, 106, and 107 are just some of the range of locations useful for biosensors. For example, biosensors can also be positioned on or near the temple, earlobes, axillary regions, fingertips, or feet. As shown, there is a considerable area of the body around each of the locations 101, 102, 103, 104, 105, 106, and 107. This can make it difficult for a patient to correctly position a sensor at one of the locations 101, 102, 103, 104, 105, 106, 107, particularly when a sensor is removed from the body and should be replaced at the same position on the body.

Each of the locations 101, 102, 103, 104, 105, 106, and 107 corresponds to a respective region of the body in which sensor (e.g., physiological parameter) measurements can be taken. The size of the region depends on the type of sensor and the location on the body. For example and for intraoral examinations, such as under the tongue, a sensor location can be +5 mm in any direction with respect to a selected reference point. Other biosensors such as heart rate and ECG sensors can be positioned within 10 mm of a selected reference point (e.g., the location 102). Still other sensors, such as those for measuring motion or activity (e.g., accelerometers) can be positioned within 50 mm of a selected reference point.

Figure 2A:
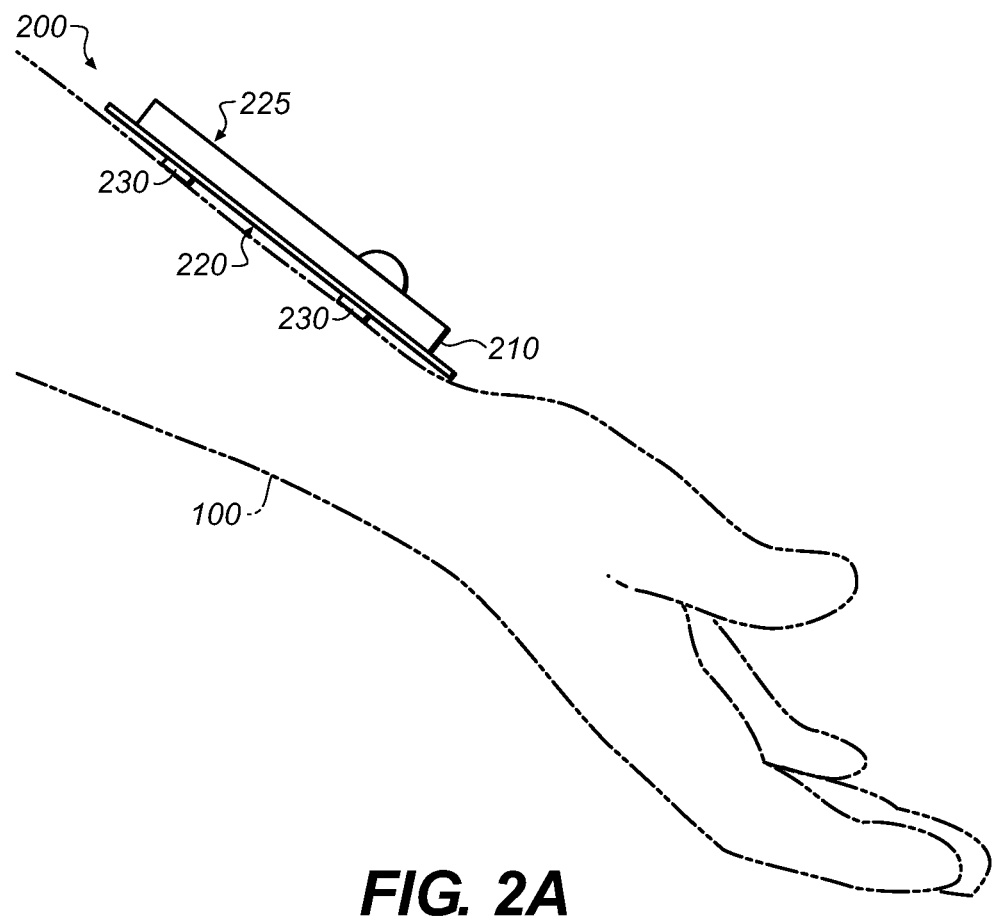
FIGS. 2A-2C are a perspective view, a rear view, and a front view, respectively, of an exemplary biosensor, showing components of the biosensor according to various embodiments.

FIG. 2A is a perspective view of an exemplary sensor 200 arranged over a body 100 (shown in phantom) to sense a physiological property thereof (e.g., potential or oxygen saturation). In this specific example, the sensor (also synonymously referred to as a "biosensor") 200 are placed over a wrist location, identified as location 106 according to FIG. 1. The sizing of the sensor 200 as shown is to provide a clear indication of the salient features. To that end, FIG. 2A is not necessarily drawn to scale and should not be relied upon for sizing or dimensional purposes. According to this exemplary embodiment, a sensor body 210 is defined by a skin-facing surface 220 and an opposing surface 225 that is visually accessible to a caregiver (not shown). The skin-facing surface 220 is arranged over the body 100 in which a plurality of conducting elements, e.g., sensor contacts 230, are disposed in spaced relation at least partly on the skin-facing surface 220. The term "skin-facing" refers to surfaces that face the subject's body. For example, sensors used in the mouth or over the eye can have skin-facing surfaces 220 facing mucous membranes and the cornea, respectively, instead of the epidermis. For purposes of this embodiment, the sensor contacts 230 form conducting elements through which a physiological property is sensed. The manner of conduction as defined herein can assume many forms such that the sensor contacts 230 can be conductive to optical energy, electrical energy, heat, or other physical characteristics or forms of energy. Throughout this disclosure, measurements made using the sensor 200 can be stored, and can be stored in association with, e.g., measurement timestamps, information about measurement devices (e.g., a serial number of the sensor 200), or information regarding the environmental conditions around the body 100 at the time of measurement. The sensor 200 can be any suitable size, e.g., blood-pressure-cuff size or fingertip-sized.

Figure 2B:
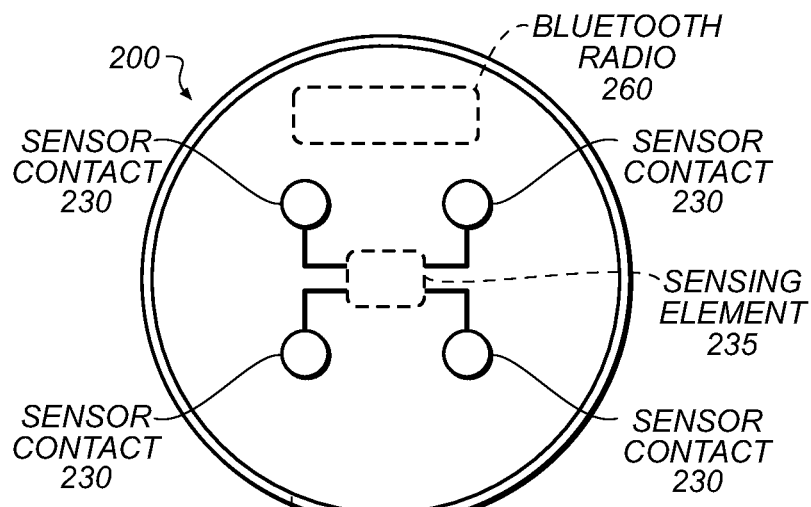

FIG. 2B is a rear facing view of the exemplary sensor 200. A sensing element 235 is connected to the spaced set of sensor contacts 230. According to this specific version, a total of four (4) sensor contacts are shown in spaced relation along the skin facing surface of the sensor 200 wherein the sensing element 235 is disposed between the various sensor contacts 230 and substantially in the center of the skin facing surface 220. This number and positioning can be suitably varied, however, depending upon the application and the physiological or other parameter being measured or monitored. The sensing element 235, using the surrounding sensor contacts 230, is configured to detect a signal representative of a physiological parameter of the body 100, FIG. 2A, facing the skin-facing surface 220. An adhesive layer 270 can be coated over or otherwise affixed to the skin-facing surface 220 to at least temporarily hold the sensor 200 to the body 100. The adhesive layer 270 can include a conductive adhesive to affix the sensor 200 to the body 100 and permit the sensor contacts 230 to effectively contact the body 100. Alternatively, the sensor 200 can be integrated into a body-worn watch, wristband, ring band, or other garment. The sensor contacts 230 can convey any desired type of energy, e.g., thermal, electrical, optical, or acoustic, between the body 100 and the sensing element 235. In at least one embodiment, the sensing element 235 detects a physiological property without connection with the sensor contacts 230. For example, the sensing element 235 can include an accelerometer to measure body motion.

Still referring to FIG. 2A, the herein described sensor 200 further retains a wireless radio, such as a BLUETOOTH radio 260 (shown here in phantom). As discussed in a later portion, other types of radio or wired or wireless transceiver can be alternatively used in lieu of the BLUETOOTH radio 260. The physiological parameter being measured by the sensor 200 can be but is not limited to blood pressure, pulse rate, pulse wave, skin conductance, galvanic skin response, temperature, electrocardiogram signal, electroencephalogram signal, electromyogram signal, heart rate variability, respiration, or other parameters. Additionally, the physiological parameter can also be blood glucose concentration, e.g., measured using an invasive or noninvasive continuous glucose monitor, or using an episodic glucose meter.

Figure 2C:
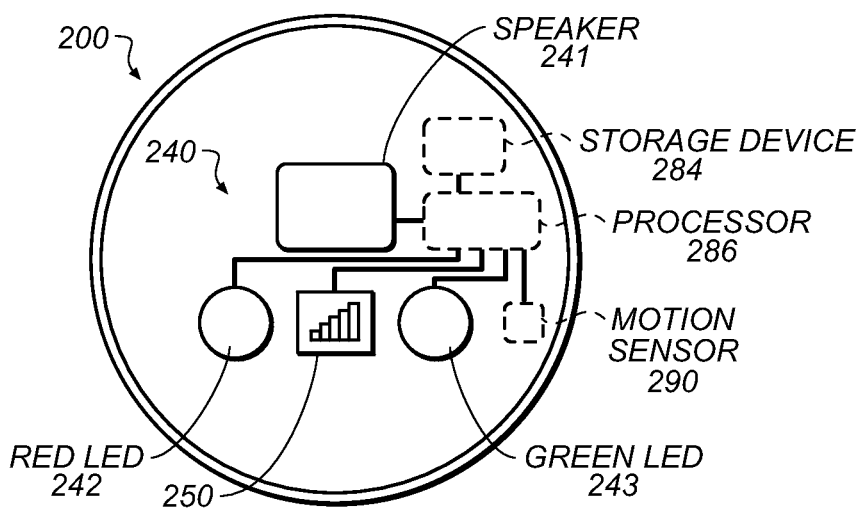

FIG. 2C is a front facing view of the exemplary biomedical sensor 200. An indicator 240 is spaced apart from the skin-facing surface 220, FIG. 2A. In other examples, the indicator is absent from the sensor 200 or is arranged over the skin-facing surface 220. In the exemplary embodiment shown, the indicator is mounted to the surface 225 and opposed to the skin facing surface 220. The indicator 240 can include one or more of a speaker 241, an LED (e.g., a red LED 242 or a green LED 243), and a segmented display 250. The indicator 240 can also or alternatively include a vibratory or light- or sound-emitting element inside the sensor body 210. For example, a light inside the sensor body 210 could emit light through a window (not shown) provided on the opposed surface 225 of the sensor 200. The indicator can be used to indicate whether the sensor 200 is correctly positioned. Examples of various indications of correct sensor positioning can include illumination from a green LED 243, pleasant audible tones from the speaker 241, and strong (or weak or absent) vibratory signals. Similarly, examples of various incorrect sensor positioning can include illumination by the red LED 242, unpleasant audible tones from the speaker 241, and weak (or strong) vibratory signals.

According to this exemplary embodiment, a storage device 284 provided in the sensor 200 stores a physiological model. Alternatively and discussed in other embodiments, the storage device could also be separate from the sensor and coupled therewith. A processor 286, also retained within the sensor 200, is coupled to the sensing element 235, FIG. 2B, the indicator 240, and the storage device 284. The processor 286 determines a quality of sensor placement by comparing the signal representative of the physiological parameter of the body 100. FIG. 2A, to the stored physiological model, e.g., by executing stored program instructions, as discussed below. The processor 286 then operates the indicator 240 to provide a human-perceptible indication of the determined quality. In this way, the sensor 200 can provide the user feedback regarding the positioning of the sensor 200.

It is generally recognized that patients bodies change physiologically over time, e.g., due to aging. In various embodiments, the processor 286 is further configured to update the stored physiological model using the representative signal provided by the sensor element 235, FIG. 2B, if the comparison indicates the detected physiological parameter corresponds to the stored physiological model. In this way, the stored physiological model can be updated to follow gradual shifts or long-term trends, reducing the incidence of false negatives (indications a correctly-placed sensor is not correctly placed) and still maintaining the usefulness of the model for detecting incorrect sensor placements.

Some common sensor-placement errors can be detected using data other than the signal representative of the physiological parameter of the body 100. For example, certain sensors are designed to be worn throughout the day. In the course of everyday activity, a sensor disposed on the arm of a subject will tend to move in a very different way than a sensor disposed on either the leg or the torso. That is, sensors on the torso will typically tend to move either vertically or horizontally at any given time, and will also tend to move generally in one direction. Sensors disposed on the hand, however, will tend to remain within a narrow area, or undergo oscillatory motion superimposed on a directional trend (e.g., while walking). Motion data exhibiting these differences can be used to determine sensor placement.

Still referring to FIG. 2C, the herein described sensor 200 further includes a motion sensor 290 (shown in phantom), such as a one-, two-, or three-axis accelerometer. The storage device 284 can further store a motion model corresponding to a selected location on the body 100, e.g., one of locations 101, 102, 103, 104, 105, 106, or 107, all FIG. 1. The processor 286 is further configured to record motion data from the motion sensor 290, compare the recorded motion data to the stored motion model, and then provide a human-perceptible indication of a result of the comparison. This latter indication can be provided using the indicator 240, as discussed herein. For purposes described herein, the storage device 284 can store multiple motion models corresponding to different locations on the body, and the processor 286 can compare the motion data to one or more of the models to determine which model (and thus which location) most closely match the motion data.

In several of these aspects, the processor 286 is further configured to provide a human-perceptible indication of the selected location if the recorded motion data does not correspond to the stored motion model. The indication can be provided, e.g., via a user interface device 640, discussed below. The indication can also be provided using arrows (not shown) on the sensor 200, such as using a display, to indicate the direction the user should move the sensor 200 to reach the selected (e.g., preferred) location.

Figure 3:
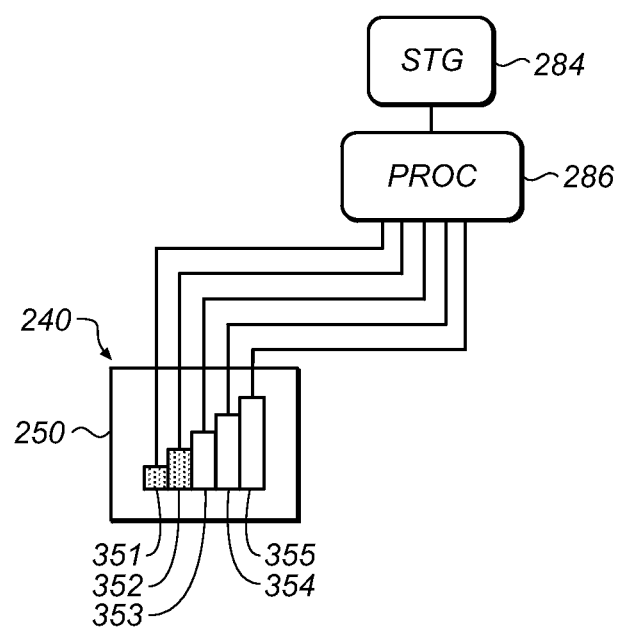
FIG. 3 is a diagram of an exemplary indicator and related components.

FIG. 3 is a diagrammatic view of an exemplary indicator 240 and related sensor components. The illustrated indicator 240 includes a segmented display 250 having segments 351, 352, 353, 354, and 355. In this example, the segments 351, 352, 353, 354, and 355 are arranged similarly to a conventional signal-strength indicator for a mobile telephone. This arrangement is referred to herein as "sensor bars" or "sensor strength bars." Analogous to providing strength of signal indication in a mobile telephone, having more of the segments 351, 352, 353, 354, and 355 illuminated provides a similar indication as to the determined quality of sensor placement. Using sensor bars advantageously provides information regarding placement in a manner many users are trained to associate with position. A user accustomed to walking or turning to improve mobile telephone reception, as indicated by bars for signal strength on the screen of the mobile telephone, can readily comprehend that a sensor should be moved around the body to improve placement quality, as indicated by the sensor bars.

In general, in various embodiments, the indicator 240 includes a plurality of separately-activatable visual indicators, e.g., segments 351, 352, 353, 354, and 355. The processor 286 determines the quality using the model from the storage device 284, as discussed above. The processor 286 then activates a selected number of the visual indicators (e.g., segments 351, 352, 353, 354, and 355) to provide the human-perceptible indication, the selected number correlated with the determined quality. The segments 351, 352, 353, 354, and 355 can be arranged in configurations other than with progressively-increasing lengths. For example, each of the segments 351, 352, 353, 354, and 355 can have the same dimensions. It is not required that the processor 286 illuminate the segments 351, 352, 353, 354, and 355 sequentially or in any particular order, although both of those options are contemplated herein. In other examples, the indicator 240 includes a seven-segment or other visual display configured to display a numeric or textual representation of the determined quality.

In an example, the processor 286 is configured to activate none of the visual indicators, e.g., none of the segments 351, 352, 353, 354, and 355, if the signal corresponds to an absence or failed detection of the physiological parameter. For example, if the sensing element 235 is not able to detect the physiological property, perhaps because the sensor 200 is not disposed over the body 100, the processor 286 can activate none of the visual indicators. The processor 286 is further configured, in this example, to activate a selected first positive number of the visual indicators if the signal is detected but is not consistent with the physiological model. For example, if a transmissive optical sensor is used in a reflective configuration, the sensing element 235 may detect light and provide a signal, but that signal will have very different properties (e.g., amplitude and propagation delay) than indicated by the stored physiological model. The processor 286 can be further configured to activate a selected second positive number of the visual indicators if the signal is detected and is consistent with the physiological model. According to this example, the selected second positive number is greater than the selected first positive number.

According to the exemplary embodiment and specifically using the segments 351, 352, and 353, the processor 286 can be configured to illuminate any of the following combinations: (a) none of the segments 351, 352, 353 if the signal is not detected; (b) the segment 351 if a signal is detected intermittently but the signal is not continuously present, or if the signal does not correspond to the physiological model; (c) the segments 351, 352 if the signal is detected and is regularly present (possibly with the exception of occasional noise or signal dropouts), and the signal conforms to the physiological model when the signal is present; or (d) the segments 351, 352, 353 if the signal is consistently present and conforms to the physiological model. In various examples, the signal is consistent with the physiological model if 95% of the data points of the signal are within a corresponding point on the physiological model, ±30% or ±20%. Other signaling or indicating variants are herein contemplated.

As discussed above, motion data can also be used. For example, the processor 286 can be configured to illuminate none of the segments 351, 352, 353, 354, 355 if recorded motion data does not correspond to that of the motion model stored, for example, in storage device 284.

Figure 4:
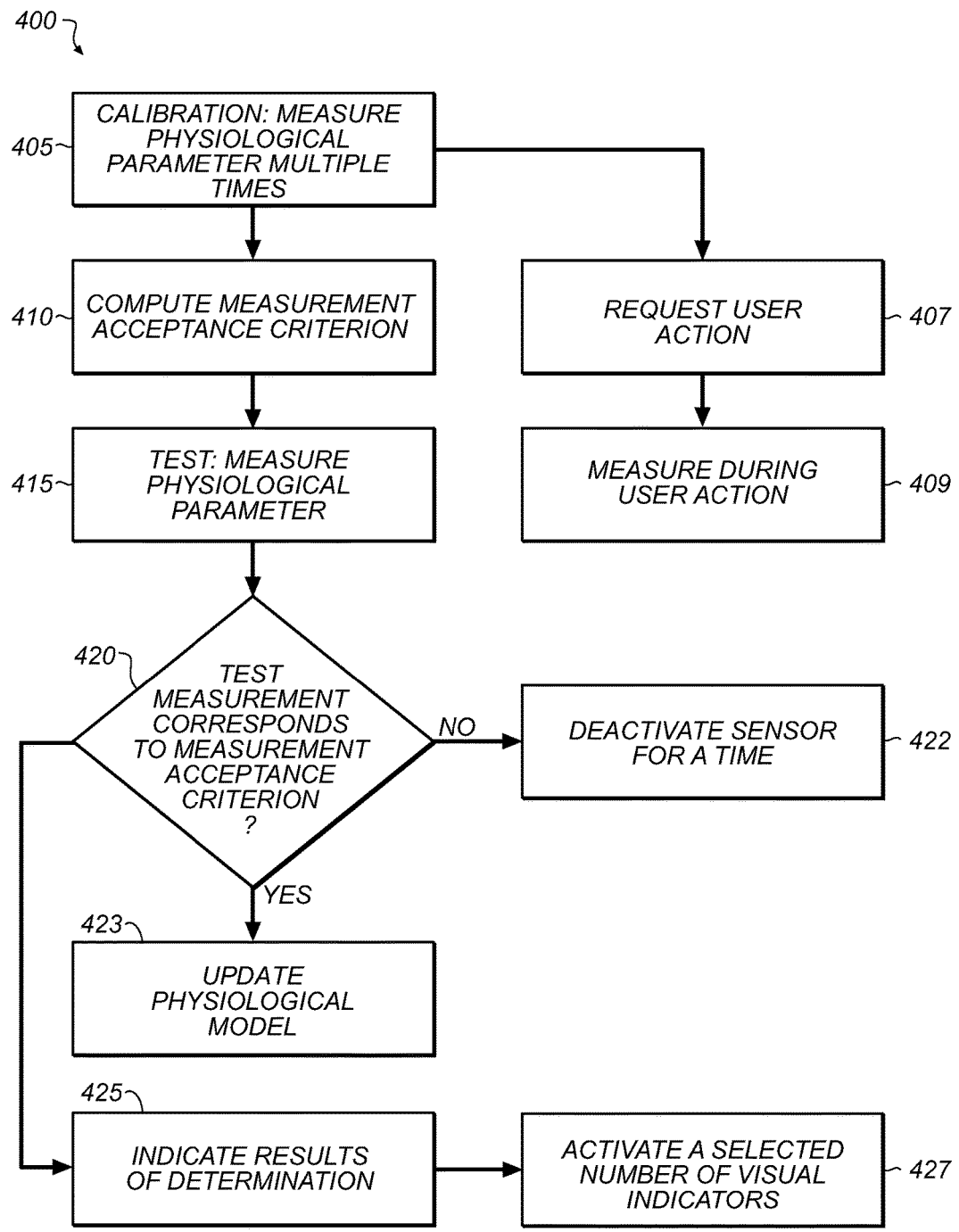
FIGS. 4 and 5 are flowcharts illustrating exemplary methods for measuring a physiological parameter of the body of a user.

FIG. 4 is a flowchart illustrating exemplary methods for measuring a physiological parameter of the body of a user. The methods can include automatically performing steps described herein using a processor. For purposes of an exemplary embodiment, processing of flowchart 400 begins with step 405. For clarity of explanation, reference is herein made to various components shown in FIGS. 1-3 that can carry out or participate in the steps of the exemplary method. It should be noted, however, that other components can be used; that is, the exemplary method is not limited to being carried out by the identified components.

Step 405 is a calibration step in which the physiological parameter of the body 100, FIG. 1, is measured a plurality of times using a sensor 200. FIG. 2A, to provide respective measurements. The calibration measurements can be taken over any span or amount of time, at regular intervals or not, with the sensor 200 in a single location on the body 100, in different locations, or at a reference position. In various embodiments, step 405 includes asking the user for information about the location of the sensor, e.g., by presenting a generic image of the body 100 on a touchscreen and asking the user to touch the screen to indicate the location of the sensor. The location can be stored in association with the respective measurements. The processor 286 can customize the generic image using data collected from the user, e.g., in steps 550 or 560, FIG. 5.

In step 410, using the processor 286, FIG. 2C, a measurement acceptance criterion is automatically computed using the respective measurements. The measurement acceptance criterion can include limits on the noise, amplitude, values, envelope, frequency, spectrum, or other properties of the measurements, taken in aggregate. In an example, the measurement acceptance criterion is computed as the envelope of the measurements. In another example, the measurements are aligned in time, e.g., each measurement is a time series of a blood pressure signal starting from the dicrotic notch. In this example, the measurement acceptance criterion is the mean±1σ or ±2σ at each sample of the time series. In another example, the measurement acceptance criterion is detection of the dicrotic notch in the arterial pressure signal. If the notch is not detected, the sensor 200 is not correctly positioned. Detection of the notch can cause the processor 286 to activate two or three bars on a three-bar segmented display 250. In at least one example, the measurement acceptance criterion is determined at least in part based on the location received from the user in step 405. For example, if the user indicates that a blood-oxygen sensor has been placed on a pointer finger, the measurement acceptance criterion can be determined using stored representative data of variation at the pointer fingertip. In various embodiments, the measurement acceptance criterion can be determined for a secondary sensor or any of multiple sensors that work together, e.g., multiple ECG electrodes.

The measurement acceptance criterion can be one element of the physiological model stored in the storage device 284, FIG. 2C. The physiological model can also include data from sensors other than the sensor 200 measured during the calibration step 405. The physiological model can include data from multiple sensors so that only certain combinations of ranges of readings from the various sensors conform to the physiological model.

Various sensors are designed for measuring the body under specific conditions. The calibration can thus be performed under those conditions. Specifically, in various embodiments, the calibration step 405 includes a step 407 of presenting an indication via a user interface (e.g., the user interface device 640, FIG. 6) that the user should perform a specific action, and a step 409 of measuring the physiological parameter while the user performs the action. Examples of specific actions including standing still, sitting, walking, and jogging. For example, the sensor can be a waist- or wrist-mounted motion sensor and the activity is walking. The measurement acceptance criterion thus corresponds to motion of the body part carrying the sensor. This correspondence permits measuring gait while walking, and disregarding data collected while standing still, thereby reducing measurement noise. According to another example, the sensor is a heart rate monitor, the activity is jogging, and the measurement acceptance criterion corresponds to heart rate ranges measured during that type of exercise.

In various aspects, step 407 includes selecting a recommended user action based on sensor data or user data. For example, placement ratings received in step 550 (FIG. 5, discussed below) and medical-condition indications received in step 560 (FIG. 5, discussed below) can be used to select the user action. Information such as whether the user is handicapped and the user's regular level of exercise can be used to select an activity that wilt provide meaningful data without laying undue burden on the user. Data from a prior calibration step 405 can also be used.

Step 415 is a testing step in which the physiological parameter of the body is measured using the sensor 200 to provide a test measurement. Step 415 can be performed, e.g., at regular intervals or on demand.

In decision step 420, the processor 286 automatically determines whether the test measurement corresponds to the measurement acceptance criterion obtained from the computing step 410. In various examples, if the measurement acceptance criterion is an envelope, the test measurement corresponds to the criterion if the points of the test measurement are within the envelope, or if 95% or 99% of the points are within the envelope. Similarly, a test measurement corresponds to a range criterion (e.g., mean±σ) criteria if each point falls (or a selected percentage of the points fall) within the appropriate range. Continuing the blood-oxygen example above, if the user indicates that the sensor is on a pointer finger but the data are more consistent with middle-finger readings than pointer-finger readings, the measurement will not correspond to the measurement acceptance criterion determined for the pointer finger.

In step 425, the processor 286 automatically operates the indicator 240 of the sensor in order to provide a human-perceptible indication of the results of the determining step. If the test measurement does not conform to the measurement acceptance criterion, it may be that the sensor 200 is not in the correct location on the body 100. Accordingly, the processor 286 can illuminate the red LED 242, FIG. 2C, or otherwise indicate to the user or a caregiver or HCP that the sensor position should be checked. In various aspects, if the measured signal has high quality (e.g., the noise levels are low and there are few transients present) but the data are out of the range of the measurement acceptance criterion, an indication can be presented that the user may consider it worthwhile to seek medical advice. For example, if the user's body temperature begins to trend upward smoothly and passes the upper limit of the measurement acceptance criterion (e.g., 105° F.) while still moving smoothly and consistently, the user may wish to determine whether the user has a severe fever.

In various aspects, the processor 286 stores the results of the determination and an indication of the location of the sensor, e.g., in step 425. This stored data can be used in step 540, FIG. 5, discussed below, in determining a subsequent sensor site. The results and the test-measurement data can be stored, e.g., for each measurement, or only for test measurements determined not to conform to the measurement acceptance criterion.

In various examples such as those described above with reference to FIG. 3, the indicator 240 includes several separately-activatable visual indicators. In these examples, step 425 can include step 427. In step 427, the processor 286 activates a selected number n of the visual indicators (e.g., some or all of segments 351, 352, 353, 354, and 355, FIG. 3) to provide the human-perceptible indication. The selected number n can be correlated with the results of the determining step, e.g., in a sensor bars configuration such as that discussed above. In an example, n is correlated with, e.g., proportional to, the percentage p), 0%≤p≤100%, of data points in the test measurement that meet the measurement acceptance criterion (e.g., an envelope). The proportionality can be, e.g., linear (e.g., four bars, with n such that p≥n×4) or logarithmic four bars, with n=4 for p≥99%, n=3 for p≥96%, n=2 for p≥90%, n=1 for p≥68%, and n=0 for p<68%).

Steps 415, 420, and 425 can be repeated as desired, at regular or irregular intervals, or on demand, to take measurements. For example, a blood pressure sensor 200 can be automatically activated every five minutes or every ten minutes to collect a measurement. If the test measurement does not conform to the measurement acceptance criterion, a care provider can be notified. Alternatively or additionally, the user can be notified and the test measurement flagged as being non-conforming. Non-conforming test measurement data can be disregarded, e.g., when computing historical averages from recorded test measurements.

When the test measurement does correspond to the measurement acceptance criterion, step 423 can follow step 420. In step 423, as discussed above, the measurement acceptance criterion or other aspects of the physiological model are updated using the test measurement. According to various embodiments, step 423 can also be performed intermittently, once per day, once per session of measurements, or at other intervals. A session of measurements can be a time span in which numerous measurements are taken with a given sensor at a given location, e.g., the time a runner spends competing in a particular race. Data from multiple test measurements can be accumulated, and step 423 can be carried out once to update the physiological model using the accumulated measurements. Processing as described above with reference to computing step 410 can be performed to update the physiological model.

In an example, the measurement acceptance criterion is that the test measurement be within 30% of the mean of the calibration measurements. Step 423 is carried out at the end of each sensor session to update information regarding that mean in the physiological model and in the measurement acceptance criterion. In this way, during the next sensor session, any deviation of more than 30% from the previous session's data will be indicated, e.g., by a drop in the number of sensor bars.

Continuing the examples discussed above with respect to steps 407 and 409, when the test measurement does not conform to the measurement acceptance criterion, the processor 286 can determine that the user is performing an activity different from the activity for which the calibration step 405 was performed, or that the sensor's environment has changed. Accordingly, decision step 420 is followed by step 422.

In step 422, the processor 286 deactivates the sensor 200 for a selected period of time. The term "deactivation" can refer to, e.g., powering down the sensor 200, or placing one or more component(s) of sensor 200 in a "sleep," "passive," or "suspend" state. In an example, a sensor 200 calibrated to measure the user's heart rate at rest can deactivate to save battery power while the user is exercising, then re-activate once the exercise is complete. In another example, as a user jogs and sweats, the sensor 200 can begin to detach from the body 100 or lose electrical contact therewith. The sensor 200 calibrated for heart rate while jogging can go to sleep or otherwise temporarily deactivate when it is no longer possible to take accurate readings. In yet another example, a photoplasmography sensor provides noisy results if skin contact is impaired as a result of mechanical stress whiles the user is jogging. The sensor can be deactivated until improved skin contact is present. In still another example, the onset of sleep can be heralded by the sensor bars (FIG. 3). As contact degrades, the bars can drop. The sensor can deactivate (sleep) when the bars drop to zero bars illuminated.

The processor 286 can periodically wake up from a sleep state and repeat steps 415 and 420 to determine whether to return the sensor 200 to normal operation. Alternatively, the sensing element 235, FIG. 2B, can be configured to provide an interrupt signal to the processor 286 to wake up the processor 286 when conditions do meet or are likely to meet the measurement acceptance criterion. Step 422 and steps 407, 409 can also be used independently of each other.

Figure 5:
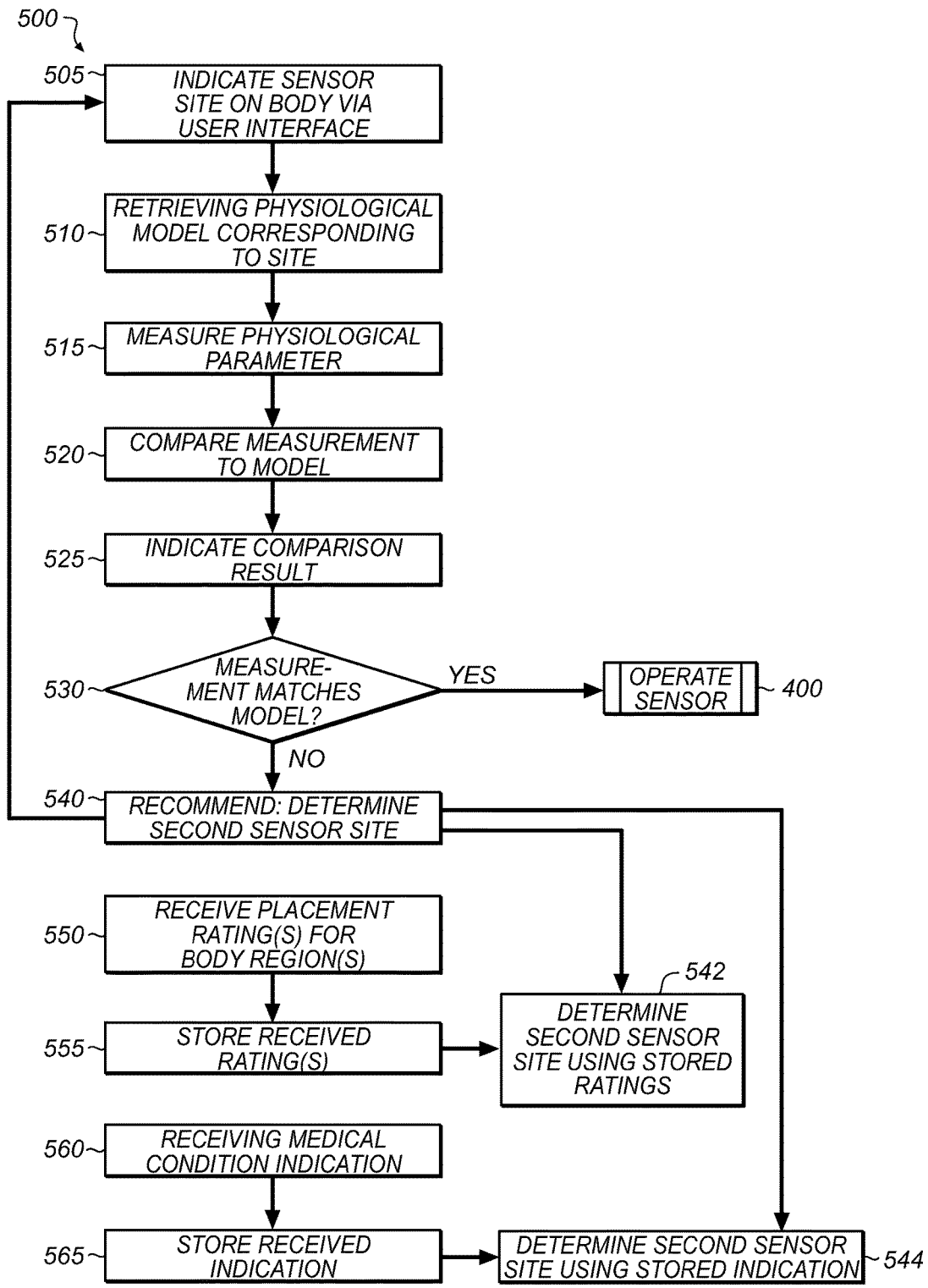

FIG. 5 is a flowchart illustrating further exemplary methods for measuring a physiological parameter of the body of a user. These methods can be used in combination with the methods shown in FIG. 4, as is discussed below. The methods can include automatically performing steps described herein using a processor. For purposes of an exemplary embodiment, processing of flowchart 500 begins with step 505. For clarity of explanation, reference is herein made to various components shown in FIGS. 1-3 and steps shown in FIG. 4 that can carry out or participate in the steps of the exemplary method. It should be noted, however, that other components or steps can be used; that is, the exemplary method is not limited to being carried out by the identified components or steps.

Figure 6:
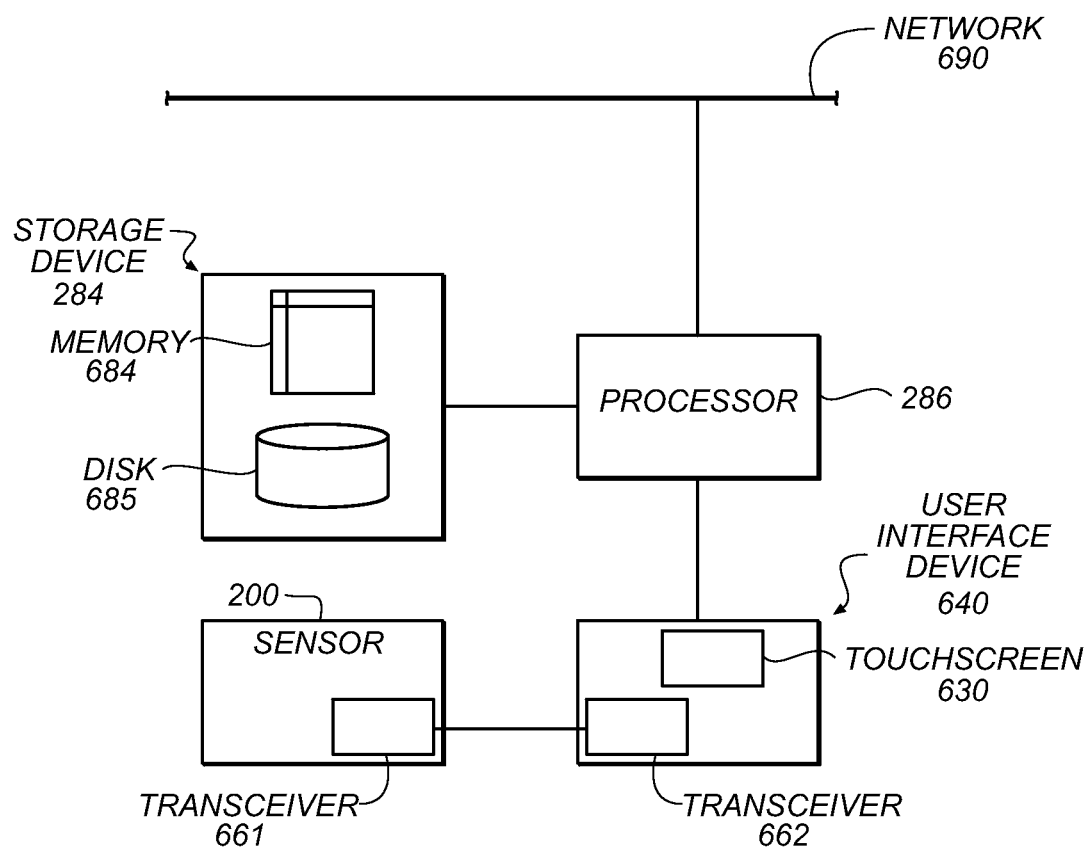
FIG. 6 is a block diagram of an exemplary system to determine optimal placement of a sensor for measuring a physiological parameter of a user.

In step 505, an indication of a sensor site on the body is presented via a user interface, e.g., a touchscreen 630, FIG. 6. For example, an image similar to FIG. 1 can be shown, with the sensor site (e.g., the location 101) visually highlighted.

In step 510, a physiological model corresponding to the indicated sensor site is retrieved from the storage device 284. The various types of models and measurement acceptance criteria discussed above, e.g., with reference to step 410, FIG. 4, can be used as part of the physiological model. For example, the physiological model for an optical pulse oximeter can indicate the wavelengths of light to be used and the range of absorptions of those wavelengths by blood with typical arterial oxygen content (e.g., 16 to 22 ml $O_2$/dL). A measurement that detects absorption outside the modeled range corresponding to the typical oxygen content can indicate that the sensor is incorrectly placed.

In step 515, the physiological parameter of the body 100 is measured using the sensor 200, FIG. 2A. This can be done as described above with reference to the sensing element 235, FIG. 2B.

In step 520, the measured physiological parameter is automatically compared to the retrieved physiological model. This can be done by the processor 286.

Step 525 is an optional second operating step. In step 525, the processor 286 can automatically operate the indicator 240 to provide a human-perceptible indication of the result of the comparing step (e.g., by lighting the red LED 242 or the green LED 243, both FIG. 2C).

In decision step 530, it is determined whether the measured physiological parameter corresponds to the retrieved physiological model. If so, measurements can be collected using the sensor 200. Steps shown in flowchart 400 can be carried out, as indicated ("operate sensor"), if not, the next step can be step 540.

Step 540 is a recommending step in which a second sensor site on the body is automatically determined, e.g., using the processor 286. Examples of how this recommendation is made are discussed below. The next step is step 505. In this way, the presenting-indication step 505, the retrieving step 510, the measuring step 515, the comparing step 520, the second operating step 525, the decision step 530, and (if necessary) the recommending step 540 can be repeated one or more times with the second sensor site or subsequent recommendations of alternative sensor sites. This advantageously permits a user to move the sensor to different locations on the body 100 and receive feedback about whether each of the locations is an appropriate site for taking measurements using the sensor 200. The motion can be user-directed, in which situation the user positions the sensor at the user's discretion, and the processor 286 determines whether the user-selected site can be used for measuring. The motion can also be system-directed, in that the processor 286 can present a series of recommended sensor sites by repeating this loop, and can collect one or more measurement(s) at each site. In either situation, the processor 286 can store measurement acceptance criteria or physiological models for each of a plurality of locations, and can recommend one of the pluralities of locations having the lowest error bands or the most consistent data.

As discussed above with reference to step 425, FIG. 4, previous measurements and related data can also be used. For example, sensor rotation can take into account locations used recently, e.g., within the last week or month. As discussed above with reference to step 405, FIG. 4, user information about the location of the sensor can also be used, e.g., for sensor rotation, or to differentiate between otherwise-equivalent locations (such as the left side of the waist vs. the right side of the waist).

In various aspects, information from the user or an HCP is used together with the physiological model in providing recommendations. In these aspects, step 540 can include one or both of steps 542, 544. Step 542 is preceded by steps 550, 555; step 544 is preceded by steps 560, 565.

In an example, the user provides ratings for of sensor placements in respective regions of the body. The ratings can be on any scale, e.g., (−1=bad, 0=neutral, 1=good) or 1-5 stars, one star representing the worst placement and live stars representing the best placement. Each rating indicates the user's preference for placing a sensor (whether of a specific type or of any type) in the corresponding region of the body. In an example, a user may not wish to wear a gait sensor on the wrist. For that user, the combination of (gait sensor, wrist) has a low rating (e.g., *). The combination of (gait sensor, waist) can have a high rating (e.g., ***). In various embodiments, unrated combinations are assigned a default rating. If the default rating is *, then (gait sensor, waist) will rank above (gait sensor, wrist with a * rating. The processor 286 can solicit ratings via a questionnaire or in other ways. Ratings can represent the level of comfort or discomfort the user experiences when a particular sensor is attached to a particular region of the body.

In various embodiments, in step 550, one or more user indication(s) of respective rating(s) of sensor placement(s) in respective region(s) of the body is/are received via the user interface (e.g., the touchscreen 630, FIG. 6). In step 555, the received user indication(s) are stored in the storage device 284.

In step 542, the second sensor site is determined using the stored user indication(s) (rating(s)). For example, the processor 286 can sort the possible sites for a particular sensor by rating and suggest them as the second sensor site in order from highest-ranked to lowest.

In other examples, the user or HCP provides medical information useful for determining the second sensor site. For example, for a person whose left leg has been amputated, no site on the left leg should be determined as the second sensor site, regardless of which sensor is to be used or how poorly any other site is rated. This is referred to herein as a rating of "N" for any sensor on the left leg; "N" represents any flag value distinct from any possible rating. Moreover, some sensors must be moved between sensor sites periodically; this is referred to as "rotation." For example, continuous glucose monitor (CGM) sensors include a needle that punctures the skin, and are rotated periodically to permit the skin to heal. The medical information can indicate that rotation is required for a particular sensor.

In various embodiments, and according to step 560, an indication of a medical condition of the user is received via the user interface. In step 565, the indication is stored in the storage device 284. The indication can be provided by answering a questionnaire presented via the user interface. The indication can also be provided indirectly. Examples of medical condition indications include height, weight, and the names of any diseases or long-term conditions. In an example, the processor 286 receives an image of the user's body 100 via the user interface. The processor 286 analyzes the image to determine whether any limbs are missing, and stores the results of any such determination. Some types of optical sensors are calibrated to particular skin tones; the processor 286 can also analyze the image to determine the user's skin tone to provide more accurate results with such sensors.

In step 544, the second sensor site is determined using the stored indication. Any (sensor, site) pair with a rating of N is omitted from consideration to be the second sensor site. Steps 544 and 542 can be combined; after rating-N pairs are removed, the remaining pairs for the appropriate sensor type can be sorted by rating.

FIG. 6 is a block diagram of an exemplary system to determine optimal placement of a sensor for measuring a physiological parameter of a user using sensors (e.g., biosensors) as described herein. The sensor 200 has a sensing element 235, FIG. 1, configured to measure a physiological parameter. The sensor 200 also has a first transceiver 661 configured to communicate the measurement. A BLUETOOTH radio 260, FIG. 2B, is an example of a first transceiver 661.

A user interface device 640 includes a second transceiver 662 configured to receive the measurement from the first transceiver 661. Communication between the transceivers 661, 662 can be unidirectional, half-duplex bidirectional, or full-duplex bidirectional. The user interface device 640 can be, e.g., a smartphone, tablet computer, or personal computer running software (e.g., a smartphone app) to receive data from the sensor 200 and optionally control the operation of the sensor 200. The user interface device 640 can include a mouse, a keyboard, another computer (connected, e.g., via, a network or a null-modem cable), a microphone and speech processor or other device(s) for receiving voice commands, a camera and image processor or other device(s) for receiving visual commands, e.g., gestures, or any device or combination of devices from which data is input to the processor 286.

The processor 286 is associated with the user interface device 640. The processor 286 is configured to automatically determine, using the received measurement, whether a sensor position over the body at a time corresponding to the received measurement meets a selected acceptance criterion. This can be done as discussed above with reference to steps 415, 420, FIG. 4, and steps 510, 515, 520, 530, FIG. 5. The processor 286 is further configured to present sensor-position feedback to the user via the user interface device 640 if the received measurement does not meet the selected acceptance criterion. For example, the user interface device 640 can include the touchscreen 630 configured to present the sensor-position feedback. The touchscreen 630 can also serve as an indicator 240, as discussed above with reference to FIG. 2C.

In an example, the user interface device 640 (e.g., a smartphone) is separate from the sensor 200. The first and second transceivers 661, 662 can include respective radio-frequency communications transceivers, e.g., for WIFE BLUETOOTH, ZIGBEE, ALOHA, or other radio communications protocols; or infrared (e.g., IrDA) or other optical- or near-optical-wavelength protocols. The first and second transceivers 661, 662 can also or alternatively include respective wired-communications transceivers, e.g., for ETHERNET, FIREWIRE, I$^2$C, or SPI. In another example, the user interface device 640 is integrated with the sensor 200. The user interface device 640 can also or alternatively communicate with the sensor 200 via a cloud or other network service. The processor 286 and the storage device 284 can be incorporated within the user interface device 640 or arranged separately therefrom.

In various aspects, the processor 286 is configured to receive a plurality of measurements from the sensor 200 via the first and second transceivers 661, 662. The processor 286 is configured to, concurrently with receiving the measurements, present respective sensor-position feedback for each of the plurality of measurements via the user interface device 640. In this way, a user can move the sensor to different locations on the body 100 and receive feedback before adhering the sensor 200 to the body 100. The feedback can be provided via the indicator 240 on the sensor 200 instead of or in addition to being provided via the user interface device 640. Feedback on the sensor 200 permits the sensor 200 to operate in a manner similar (from the user's perspective) to a metal detector or stud finder. The user can sweep the sensor 200 across the body 100 until, e.g., the sensor bars on the segmented display 250, or the green LED 243, or a tone on the speaker 241, all FIG. 2, indicates that the sensor 200 is positioned correctly. The sensor 200 can then be adhered to the body 100 at that position, e.g., by peeling a non-stick backer (not shown) off the adhesive layer 270, FIG. 2B, and pressing the sensor 200 and the exposed adhesive layer 270 against the body 100. In various examples, the non-stick backer has cutouts, recesses, or other features to permit the sensor contacts 230 to contact the skin on the body 100 even before the non-stick hacker is peeled off. These features permit the sensor to be effectively swept across the body without snags while taking measurements, and further permits measurements to be taken once the sensor is applied to the body 100.

In other examples, the processor 286 is configured to store the measurements and present the feedback at a later time than the time of measurement, e.g., at the request of a user. The processor 286 can also store real-time feedback while presenting it or shortly thereafter.

In various embodiments, an electrode, such as an electrode used in testing connectivity of ECG-measurement units, placed on the body at a central location sends out a signal with a selected waveform. The sensor 200 detects the signal after the signal travels through the body. The processor 286 determines the electrical conductivity of the body using the received signal. In various examples, the processor 286 determines the distance from the electrode or the position of the sensor 200 with respect to the electrode. The processor 286 then presents an indication of the determined location, e.g., via the user interface device 640 or the indicator 240. The processor 286 prompts the user for confirmation that the determined location is correct. The processor 286 receives and stores the user's answer. If the determined location is not correct, the processor 286 can also prompt for, receive, and store an indication from the user of the correct location. The determined or correct location can be used along with measurements of the waveform to determine the position of a sensor newly-placed on the body.

In an example, the centralized electrode sends out an electrical signal to the sensor. The impedance is measured between centralized electrode and the sensor. An estimated distance between the electrode and the sensor is calculated using the measured impedance. The impedance can also be measured using the patient height and weight, in a manner similar to a bioelectrical impedance analyzer (BIA), e.g., as used for estimating body fat percentage. BIAs typically pass a current through the body via two electrodes and measure the voltage developed across those electrodes by the impedance of the body. The measured impedance can be correlated with the patient's height, weight, sex, and other factors to determine a sensor-to-electrode spacing corresponding to a particular measured impedance.

Various embodiments with peel-off backers require lifting the sensor and replacing it in the same location. To facilitate this, various embodiments of sensors 200 include a marking implement (not shown) using semi-permanent (e.g., India ink) material. A button or other control (not shown) on or in the sensor 200 causes the marking implement to protrude from the sensor 200 to leave a mark on the body, e.g., a non-toxic-ink splotch. This mark serves as an alignment feature for replacing the sensor in the correct location after peeling off the backer.

Various embodiments include a method of recommending a sensor site on a body, the method comprising presenting an indication of a location on the body to place the sensor; measuring a physiological parameter of the body using the sensor placed substantially in the indicated location; automatically determining whether the indicated location is a recommended sensor site using a processor based on the measured physiological parameter, and presenting an indication of the result of that determination using an indicator of the sensor; and, if the indicated location is not a recommended sensor site, automatically determining a second location on the body and presenting an indication of the second location.

Various embodiments advantageously use multiple inputs (e.g., physiological, modeled, and user data) to determine where to place the sensor 200. Feedback mechanisms (e.g., visual, audible, or tactile, on the sensor 200, the user interface device 640, a computer, or a smartphone) communicate status information regarding the positioning in a readily-comprehensible form. If these multiple inputs are not consistent (e.g., accelerometer data corresponds to the leg but user data indicates the sensor 200 is attached to an armband), various embodiments can query the user for updated information and present indications of the system's understanding of the sensor position. Various embodiments advantageously permit the sensor to be positioned consistently over extended periods of time, even when a sensor is removed and replaced.

Various embodiments monitor sensor performance, e.g., using measurement acceptance criteria as described above with reference to FIG. 4. This can be done as part of sensor position determination, or the two can be done independently.

Still referring to FIG. 6, the processor 286 includes one or more data processor(s) that implement processes of various embodiments described herein. A "data processor" is a device for processing data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise. The phrase "communicatively connected" includes any type of connection, wired or wireless, between devices, data processors, or programs in which data can be communicated. Subsystems such as the storage device 284 and the user interface device 640 are shown separately from the processor 286 but can be stored completely or partially within the processor 286.

The storage device 284 includes or is communicatively connected with one or more tangible non-transitory computer-readable storage medium(s) configured to store information, including the information needed to execute processes according to various embodiments. The term "device" does not imply that storage device 284 include only one piece of hardware that stores data. A "tangible non-transitory computer-readable storage medium" as used herein refers to any non-transitory device or article of manufacture that participates in storing instructions which may be provided to the processor 286 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM).

Embodiments of the present invention can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct the processor 286 to perform a particular series of operational steps when loaded, thereby implementing functions or acts specified herein, e.g., measuring sensor data and determining sensor sites.

In an example, the storage device 284 includes a memory 684, e.g., a random-access memory, and a disk 685, e.g., a tangible computer-readable storage device such as a hard drive or a solid-state flash drive. Computer program instructions are read into the memory 684 from the disk 685, or a wireless, wired, optical fiber, or other connection. The processor 286 then executes one or more sequences of the computer program instructions loaded into the memory 684, as a result performing process steps and other processing described herein. In this way, the processor 286 carries out a computer implemented process that provides technical effects described herein, e.g., measuring physiological properties of a patient's body. For example, blocks of the flowchart illustrations or block diagrams herein, and combinations of those, can be implemented by computer program instructions. The memory 684 can also store data used by running programs.

Program code to carry out methods described herein can execute entirely on a single processor 286 or on multiple communicatively-connected processors 286. For example, code can execute wholly or partly on a user's computer and wholly or partly on a remote computer, e.g., a server. The remote computer can be connected to the user's computer through a network 690. The user's computer or the remote computer can be non-portable computers, such as conventional desktop personal computers (PCs), or can be portable computers such as tablets, cellular telephones, smartphones, or laptops.

The user interface device 640 also can include a display device, a touchscreen, a processor-accessible memory, or any device or combination of devices to which data is output by the processor 286. In this regard, if the user interface device 640 includes a processor-accessible memory, such memory can be part of the storage device 284 even though the user interface device 640 and the storage device 284 are shown separately in FIG. 6. For example, the user interface device 640 can include one or more touchscreen(s), speaker(s), buzzer(s), vibrator(s), button(s), switch(es), jack(s), plug(s), or network connection(s).

In various embodiments, the processor 286 is communicatively connected to the network 690, e.g., via a communications interface or transceiver (not shown). The processor 286 can send messages and receive data, including program code, to and from the network 690. For example, requested code for an application program (e.g., a JAVA applet) can be stored on a tangible non-volatile computer-readable storage medium connected to the network 690. A network server (not shown) can retrieve the code from the medium and transmit it via the network 690 to the processor 286. The received code can be executed by the processor 286 as it is received, or stored in the storage device 284 for later execution.

PARTS LIST FOR FIGS. 1-6

100 body
101, 102, 103, 104, 105 locations
106, 107 locations
186 processor
200 sensor
210 sensor body
220 skin-facing surface
225 opposed surface
230 sensor contact
235 sensing element
240 indicator
241 speaker
242 red LED
243 green LED
250 segmented display
260 BLUETOOTH radio
270 adhesive layer
284 storage device
286 processor
290 motion sensor
351, 352, 353, 354, 355 segments
400 flowchart
405, 407, 409, 410, 415 steps
420 decision step
422, 423, 425, 427 steps
500 flowchart
505, 510, 515, 520, 525 steps
530 decision step
540, 542, 544, 550, 555 steps
560, 565 steps
630 touchscreen
640 user interface device
661, 662 transceivers
684 memory
685 disk
690 network While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Separate references to "an embodiment" (or "aspect" or "example") or "particular embodiments" or the like do not necessarily refer to the same embodiment or embodiments; however, such embodiments are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted. To the extent there are variations of the invention that are within the spirit of the disclosure or are equivalent to the inventions found in the claims, it is the intent that this patent will cover those variations as well.

What is claimed is:

1. A biomedical sensor, comprising:
    a) a sensor body having a skin-facing surface and an opposed surface;
    b) a plurality of conducting elements disposed at least partly over the skin-facing surface;
    c) a sensing element connected to the conducting elements, so that the sensing element detects a signal representative of a physiological parameter of a body facing the skin-facing surface using the conducting elements;
    d) an indicator spaced apart from the skin-facing surface, the indicator including plural separately-activatable visual indicators;
    e) a storage device storing a physiological model; and f) a processor coupled to the sensing element, the indicator, and the storage device, so that the processor determines a quality of sensor placement by comparing the signal to the stored physiological model and operates the indicator to provide a human-perceptible indication of the determined quality; and wherein the processor is configured to activate none of the visual indicators if the signal corresponds to an absence or failed detection of the physiological parameter; to activate a selected first positive number of the visual indicators if the signal is not consistent with the physiological model; and to activate a selected second positive number of the visual indicators if the signal is consistent with the physiological model, the selected second positive number being greater than the selected first positive number.

2. The sensor according to claim 1, wherein the physiological parameter is selected from the group consisting of blood pressure, pulse rate, pulse wave, skin conductance, galvanic skin response, temperature, electrocardiogram signal, blood glucose concentration, electroencephalogram signal, electromyogram signal, heart rate variability or combinations hereof.

3. The sensor according to claim 1, further including a motion sensor and a storage device storing a motion model corresponding to a selected location on the body, in which the processor is further configured to record motion data from the motion sensor, compare the recorded motion data to the stored motion model, and provide a human-perceptible indication of a result of the comparison.

4. The sensor according to claim 3, in which the processor is configured to provide a human-perceptible indication of the selected location if the recorded motion data do not correspond to the stored motion model.

5. The sensor according to claim 1, in which the processor is further configured to update the stored physiological model using the signal if the comparison indicates the detected physiological parameter corresponds to the stored physiological model.

6. A method of determining optimal placement of a sensor for measuring a physiological parameter of a user, the method comprising:
    a calibration step of measuring the physiological parameter of the body using a sensor a plurality of times to provide respective measurements;
    using a processor, automatically computing a measurement acceptance criterion using the respective measurements;
    a testing step of measuring the physiological parameter of the body using the sensor to provide a test measurement;
    automatically determining whether the test measurement corresponds to the measurement acceptance criterion obtained from the computing step; and
    automatically operating an indicator of the sensor to provide a human-perceptible indication of the results of the determining step.

7. The method according to claim 6, in which the calibration step comprises presenting an indication via a user interface that the user should perform a specific action, and measuring the physiological parameter while the user performs the action.

8. The method according to claim 6, in which the operating step comprises deactivating the sensor for a selected period of time if the test measurement does not correspond to the measurement acceptance criterion obtained from the computing step.

9. The method according to claim 6, in which the indicator comprises plural separately-activatable visual indicators, in which the operating step comprises activating a selected number of the visual indicators to provide the human-perceptible indication, the selected number correlated with the results of the determining step.

10. The method according to claim 6, further including:
    presenting an indication of a sensor site on the body via a user interface;
    retrieving from a storage device a physiological model corresponding to the indicated sensor site;
    measuring the physiological parameter of the body using the sensor;
    automatically comparing the measured physiological parameter to the retrieved physiological model; and
    a second operating step of automatically operating the indicator to provide a human-perceptible indication of the result of the comparing step.

11. The method according to claim 10, further including, if the measured physiological parameter does not correspond to the retrieved physiological model:
    performing a recommending step of automatically determining a second sensor site on the body; and
    repeating the presenting-indication, retrieving, measuring, and comparing steps, and the second operating step, using the second sensor site.

12. The method according to claim 11, further including receiving via the user interface one or more user indication(s) of respective rating(s) of sensor placement(s) in respective region(s) of the body and storing the received user indication(s) in the storage device, the recommending step including determining the second sensor site using the stored user indication(s).

13. The method according to claim 11, further including receiving via the user interface an indication of a medical condition of the user and storing the indication in the storage device, the recommending step including determining the second sensor site using the stored indication.

14. A system to determine optimal placement of a sensor for measuring a physiological parameter of a user, the system comprising:
    a) a sensor having a sensing element configured to measure the physiological parameter, and having a first transceiver configured to communicate the measurement;
    b) a user interface device including a second transceiver configured to receive the measurement from the first transceiver; and
    c) a processor associated with the user interface device and configured to automatically determine, using the received measurement, whether a sensor position over the body at a time corresponding to the received measurement meets a selected acceptance criterion, and, if not, to present sensor-position feedback to the user via the user interface device.

15. The system according to claim 14, in which the user interface device comprises a device separate from the sensor, and the first and second transceivers including radio-frequency communications transceivers.

16. The system according to claim 15, the user interface device including a touchscreen configured to present the sensor-position feedback.

17. The system according to claim 14, in which the processor is configured to receive a plurality of measurements from the sensor via the first and second transceivers and to concurrently present respective sensor-position feedback for each of the plurality of measurements via the user interface device.

18. The system according to claim 14, further including a storage device configured to store data representing the selected acceptance criterion.

* * * * *